United States Patent
Rognini et al.

(10) Patent No.: US 10,286,555 B2
(45) Date of Patent: May 14, 2019

(54) DEVICE, SYSTEM, AND METHOD FOR ROBOT-CONTROLLED INDUCTION OF THE FEELING OF HUMAN PRESENCE

(71) Applicant: Ecole Polytechnique Fédérale de Lausanne (EPFL), Lausanne (CH)

(72) Inventors: Giulio Rognini, Lausanne (CH); Olaf Blanke, Nyon (CH); Masayuki Hara, Tokyo (JP)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 82 days.

(21) Appl. No.: 14/973,834

(22) Filed: Dec. 18, 2015

(65) Prior Publication Data

US 2016/0176053 A1    Jun. 23, 2016

Related U.S. Application Data

(60) Provisional application No. 62/094,092, filed on Dec. 19, 2014.

(51) Int. Cl.
*B25J 3/04* (2006.01)
*B25J 9/16* (2006.01)
(Continued)

(52) U.S. Cl.
CPC ........... *B25J 9/1689* (2013.01); *A61B 5/4005* (2013.01); *A61B 5/4064* (2013.01);
(Continued)

(58) Field of Classification Search
CPC .......... B25J 9/1689; B25J 3/04; B25J 13/025; A61N 1/36082; A61B 5/4005; A61B 5/4064; A61B 5/4094; A61B 5/7275
See application file for complete search history.

(56) References Cited

U.S. PATENT DOCUMENTS

| | | | | |
|---|---|---|---|---|
| 6,123,661 | A * | 9/2000 | Fukushima | A61M 21/00 600/26 |
| 6,585,668 | B2 * | 7/2003 | Nissim | A61H 7/001 601/103 |
| 2016/0176053 | A1 | 6/2016 | Rognini et al. | |

OTHER PUBLICATIONS

M. Hara et al. "A Novel Approach to the Manipulation of Body-Parts Ownership Using a Bilateral Master-Slave System", 2011 IEEE/RSJ International Conference on Intelligent Robots and Systems Sep. 25-30, 2011, ppg. 4664-4669.*

(Continued)

*Primary Examiner* — Patrick H Mackey
(74) *Attorney, Agent, or Firm* — Andre Roland S.A.; Nikolaus Schibli

(57) ABSTRACT

A method for inducing the feeling of a presence (FoP) in a subject by using a master-slave robotic system, the method including the steps of altering a visual perception of a surrounding environment of the subject, connecting the subject with a robotic master device so that the subject can move, move on or manipulate the robotic master device, connecting the subject with a robotic slave device, making the subject move, move on or manipulate the robotic master device so that the subject is directly or indirectly touched by the robotic slave device according to a movement of the robotic master device, wherein the robotic master device and the robotic slave device are operatively connected so that the subject receives at least one of spatially and temporally conflicting sensorimotor stimulation.

16 Claims, 5 Drawing Sheets

(51) Int. Cl.
  *A61B 5/00* (2006.01)
  *A61N 1/36* (2006.01)
  *B25J 13/02* (2006.01)
  *G06F 19/00* (2018.01)
  *A61N 2/00* (2006.01)

(52) U.S. Cl.
  CPC ........ *A61B 5/7275* (2013.01); *A61N 1/36082* (2013.01); *B25J 3/04* (2013.01); *B25J 13/025* (2013.01); *G06F 19/00* (2013.01); *A61N 2/006* (2013.01); *Y10S 901/02* (2013.01); *Y10S 901/47* (2013.01)

(56) References Cited

OTHER PUBLICATIONS

G. Rognini et al. "Visuo-tactile integration and body ownership during self-generated action" European Journal of Neuroscience, vol. 37 pp. 1120-1129, 2013.*

Agid, Y. (1991). Parkinson's disease: pathophysiology. The Lancet, 337(8753), 1321-1324.

Baker, W. L., Silver, D., White, C. M., Kluger, J., Aberle, J., Patel, A. A., & Coleman, C. I. (2009). Dopamine agonists in the treatment of early Parkinson's disease: a meta-analysis. Parkinsonism & related disorders, 15(4), 287-294.

Diederich, N. J., Fénelon, G., Stebbins, G., & Goetz, C. G. (2009). Hallucinations in Parkinson disease. Nature Reviews Neurology, 5(6), 331-342.

European Search Report of EP16206649.2 dated Jun. 26, 2017.

Pagonabarraga, J., Martinez-Horta, S., Fernández de Bobadilla, R., Pérez, J., Ribosa-Nogué, R., Marín, J., . . . & Kulisevsky, J. (2016). Minor hallucinations occur in drug-naive Parkinson's disease patients, even from the premotor phase. Movement Disorders, 31(1), 45-52.

Preliminary Opinion of the European Search Authority dated Jun. 26, 2017.

Ravina, B., Marder, K., Fernandez, H. H., Friedman, J. H., McDonald, W., Murphy, D., . . . & Factor, S. (2007). Diagnostic criteria for psychosis in Parkinson's disease: report of an NINDS, NIMH work group. Movement Disorders, 22(8), 1061-1068.

Urwyler, P., Nef, T., Killen, A., Collerton, D., Thomas, A., Burn, D., . . . & Mosimann, U. P. (2014). Visual complaints and visual hallucinations in Parkinson's disease. Parkinsonism & related disorders, 20(3), 318-322.

Wood, R. A., Hopkins, S. A., Moodley, K. K., & Chan, D. (2015). Fifty percent prevalence of extracampine hallucinations in Parkinson's disease patients. Frontiers in neurology, 6.

Blanke et al., "Neurological and robot-controlled induction of an apparition," Current Biology. vol. 24, 2014, supplemental information.

Blanke et al., "Neurological and robot-controlled induction of an apparition," Current Biology, vol. 24, pp. 2681-2686, 2014.

* cited by examiner

DEVICE, SYSTEM, AND METHOD FOR ROBOT-CONTROLLED INDUCTION OF THE FEELING OF HUMAN PRESENCE

CROSS-REFERENCE TO RELATED APPLICATIONS

This patent application claims priority to the provisional patent application with the Ser. No. 62/094,092, filed on Dec. 19, 2014, the entire contents thereof being herewith incorporated by reference.

FIELD OF THE INVENTION

The invention pertains to the field of cognitive and clinical neuroscience, robotics, and human-machine interactions. In particular, the invention pertains to the field of robotic apparatuses, systems, and methods for causing a human being the feeling of a presence or of a person in close proximity.

DISCUSSION OF THE BACKGROUND

Tales of ghosts, wraiths, and other apparitions have been reported in virtually all cultures. The strange sensation that somebody is nearby when no one is actually present and cannot be seen is a fascinating feat of the human mind, and this apparition is often covered in the literature of divinity, occultism, and fiction.

Descending with his brother from the summit of Nanga Parbat, one of the ten highest mountains in the world, Reinhold Messner felt a third climber "descending with us, keeping a regular distance, a little to my right and a few steps away from me, just outside my field of vision." Messner "could not see the figure" but "was certain there was someone there," sensing "his presence." This apparition, the sensation that somebody is nearby when no one is actually present, is called the feeling of a presence, hereinafter "FoP," and has been described during periods of physical or mental exhaustion and has influenced occult literature and fiction. Although people do not see the "presence," they may describe its spatial location and frequently turn around or offer food to the invisible presence.

This condition is very different from other bodily hallucinations such as the autoscopic phenomena, which are defined as illusory own-body perceptions, during which patients experience the visual illusory reduplication of their own body in extrapersonal space. Three main forms of autoscopic phenomena have been defined: during autoscopic hallucinations, a second own body is seen without any changes in bodily self-consciousness; during out-of-body experiences ("OBE"), the second own body is seen from an elevated perspective and location associated with disembodiment; finally, during heautoscopy, subjects report strong self-identification with the second own body, often associated with the experience of existing at and perceiving the world from two places at the same time. All these conditions have been linked either to a single and hemisphere-specific lesion brain site or to disorders of multisensory integration that do not involve the sensorimotor system.

Recent developments in video, virtual reality and robotics technologies have allowed researchers to investigate the central mechanisms of bodily self-consciousness by providing subjects with ambiguous multisensory information about the location and appearance of their own body. This has made it possible to study important aspects of bodily self-consciousness, how they relate to the processing of bodily signals and which functional and neural mechanisms they may share. Using robotic technology, it has been possible to achieve specific bodily conflicts and induce predictable changes in fundamental aspects of self-consciousness by altering healthy subjects' bodily self-perception.

Although the FoP has been described in psychiatric and neurological patients, as well as in healthy individuals in different situations, its neural origin is unknown. Abnormal integration of sensorimotor signals and their cortical representations has been described in schizophrenic patients and has been associated with positive hallucinatory and delusional symptoms. According to this view, positive schizophrenic symptoms, such as alien voices and delusions of control, are caused by central deficits in integrating predicted sensory consequences of own movements and the respective reafferent signals. As a consequence, it is hypothesized that schizophrenic patients, under certain conditions, may not perceive self-generated sounds and movements as such but may misperceive them as being generated by external agents (as in the experience of alien voices or control of own movements by others), and this is corroborated by behavioral and neuroimaging investigations.

A single case report showed that electrical stimulation in temporoparietal brain cortex induces the FoP, suggesting that disturbed sensorimotor processing (tactile, proprioceptive, and motor cues) is important. However, this has not been confirmed in other patients, and the significance of these findings for the FoP in healthy subjects is unclear. There is therefore a need in the for a device, system, and method that uses the mechanisms underlying the spontaneous triggering of the FoP, or for the voluntary induction thereof, which could impact not only the basic cognitive neuroscience research and the linked disordered mental statuses, for example but not limited to schizophrenia, psychosis in major depression, depersonalization, but also other domains such as those of videogames and virtual or augmented reality.

SUMMARY

According to one aspect of the embodiments of the present invention, the surprising and unexpected discovery is provided that by using a system comprising a master device and a slave device, FoP can be induced when a subject is exposed to conflicting sensorimotor signals that are spatially and temporally incompatible with physical inputs (such as e.g. the illusion of self-touch) using well-controlled bodily stimulations. According to another aspect of the embodiments, when the subject moves or otherwise manipulates a master device that is operably connected to a slave device which maps the master device's movements. The master-slave robotic system generates a spatiotemporal mismatch between subject's movements (motor-proprioceptive signals), and the thus related master device movement, and their sensory consequence (tactile/haptic feedback generated by the slave device on the subject), which is delayed and spatially incompatible with respect to the body-related signals. This spatiotemporal conflict is resolved by the subject by generating the illusory experience that the felt touch is not caused by himself (through the master-slave system) but by another person who is touching him.

According to another aspect of the embodiments, a method is provided for inducing the feeling of a presence (FoP) in a subject by using a master-slave robotic system, including the steps of altering the visual perception of the surrounding environment of the subject, connecting the subject with at least one robotic master device so that the subject can move, move on or manipulate said at least one master device, connecting the subject with at least one robotic slave device; and make the subject move, move on or manipulate said at least one master device so that the subject is directly or indirectly touched by said at least one slave device accordingly with the master device's movement. Moreover, the master device and the slave device are operatively connected, so that the subject receives spatially and/or temporally conflicting sensorimotor stimulation.

According to yet another aspect of the embodiments of the present invention, a method is provided that can further include a step of recording physical or physiological signals from sensors placed on the slave or the master device. According to still another aspect of the embodiments, the method includes a step of altering the visual perception of the subject by blindfolding. According to a further aspect of the embodiments, the master device is a haptic device or a mobile device including a smartphone. According to an additional aspect of the embodiments, the master device is connected to a limb or a limb extremity of the subject. According to another aspect of the embodiments, the slave device is connected to a non-limb body part of the subject.

Furthermore, according to another aspect of the embodiments, the master device and/or the slave device are wearable, and the master device can a controller for a video device. According to still another aspect of the embodiments, the master device and the slave device are wirelessly connected. Moreover, according to yet another aspect of the embodiments, the method can performed in association with invasive or non-invasive brain imaging techniques (e.g. Magnetic resonance imaging, MRI; electroencephalography, EEG; near-infrared spectroscopym, NIRS; electrocorticography, ECoG) or brain stimulation techniques (e.g. Transcranial magnetic stimulation, TMS; transcranial direct-current stimulation, TDCS; transcranial pulsed ultrasound, TPU).

In addition, according to another aspect of the embodiments of the present invention, the device, system, and method can be used for the treatment or the prevention of at least some aspects of a psychiatric condition for a subject in need thereof. According to still another aspect of the embodiments of the present invention, preferably the psychiatric condition is psychosis, schizophrenia or hallucinations.

DETAILED DESCRIPTION OF THE SEVERAL EMBODIMENTS

Figure 1:
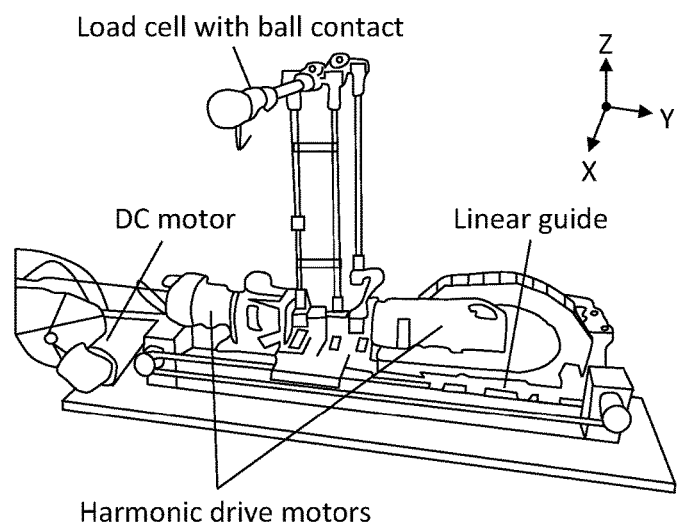
FIG. 1 depicts an embodiment of a bimanual master-slave robot.
Figure 1:
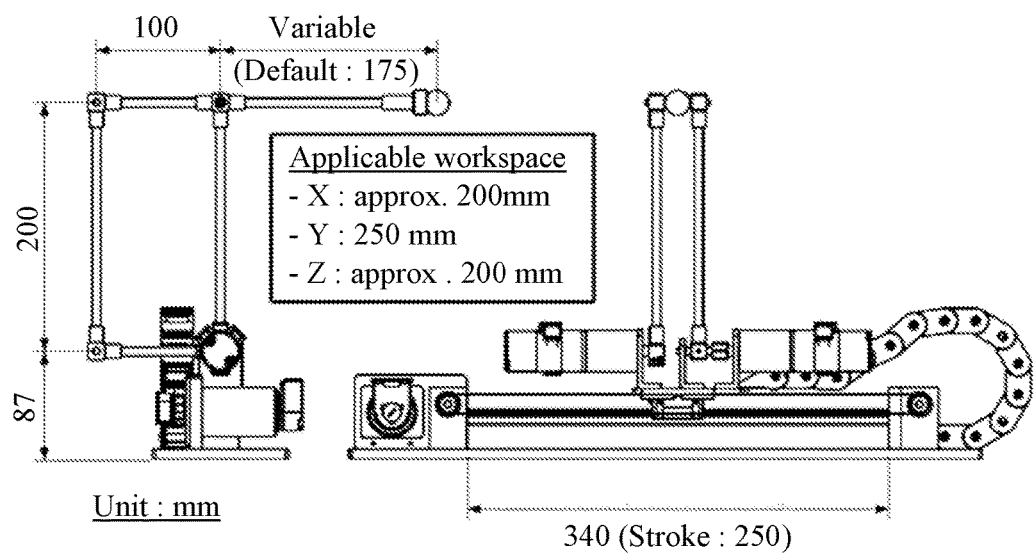

The embodiments of the present invention may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "and," and "the" include plural referents unless the context clearly dictates otherwise. Thus, for example, reference to "a device" includes a plurality of such devices and reference to "a subject" includes reference to one or more subjects, and so forth.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

According to one aspect of the present invention, a method is provided that can use a master-slave system for inducing FoP. As used herein, a "master-slave" is a model of communication where one device or process (the "master") has unidirectional control over one or more other devices (the "slave(s)"). In some systems, a master is elected from a group of eligible devices, with the other devices acting in the role of slaves. Both the master and the slave devices are preferably robotic apparatuses governed by computer-based software, and they are operatively connected among them in order to reproduce specific subject's induced movement and the related feedback. In the present disclosure, the expression "operatively connected" reflects a functional relationship between the components of the master-slave robotic system, that is, the term means that the components are correlated in a way to perform a designated function. The "designated function" is the movement of the slave device which is performed in accordance to the movement of the master device, which is in turn induced by the subject's body movement.

A person of ordinary skill in the art will appreciate that, in order to be operatively connected, a master device and a slave device do not necessarily need to be physically connected. The robotic master device and the robotic slave device can be in e.g. physical, electric or wireless connection (including WiFi, Bluetooth, magnetic, radio, telemetric, infrared, optical, ultrasonic connection and the like), as long as said connection is suitable to allow performing the designated function. In a preferred embodiment, the master device and the slave device are wirelessly connected.

A subject is placed in any suitable position (e.g. standing, sitting, lying down etc.) in an environment, and his visual perception of the surrounding environment is altered by any suitable method, such as for instance by blindfolding or by using e.g. goggles possibly comprising a head-mounted display (HMD) or even virtual reality goggles showing real or fictitious images. The subject is later connected with at least one robotic master device so that the subject can move, move on or manipulate it and at the same time he is also connected to at least one robotic slave device. In the frame of the present disclosure, the term "connected" or "connecting" or even "connection", when referred to the relationship between the master-slave system and the subject, is to be intended as a physical connection or a close proximity connection of the master and the slave device to the subject's body so that this latter can interact with them.

When the subject moves, moves on or manipulates said at least one master device preferably through limbs or extremities of his body, he is directly or indirectly touched by said at least one slave device accordingly with the master device's movement, preferably in a non-limb part of the body. The term "accordingly" means in a proper or appropriate way, i.e. in a way that suits the facts, needs, or requirements of a situation. According to some aspects, the movement of the slave device can perfectly mirror the movement of the master device both in terms of spatial and temporal coordinates, or those movements can be performed in an asynchronous or asymmetric fashion. Based on series of undue experimental results, it has been shown that during an asynchronous stimulation, i.e. a stimulation by which the touch on the subject's body provided by the slave device is temporary delayed vis-à-vis the corresponding master device's movement, a subject is able to experience a FoP.

Different types of robotic master devices can be used, as long as it is suitable to perform the designated function. A possible master device can be represented by a simple rod which is moved or manipulated by the subject. A suitable alternative for a master device for performing the claimed method is a wired glove (also known as "dataglove" or "cyberglove"), an input device for human-computer interaction worn like a glove, or even sophisticated exoskeleton limbs or the like.

Additionally or alternatively, the master device can be a controller for a video device. For instance, it can be a television controller or a videogame controller such as a joystick, a joypad, a paddle, a trackball, a throttle quadrant, a steering wheel, pedals, a mouse, a light gun or similar, a dance pad, a balance board or a microphone. Additionally, or alternatively, the master device can be a mobile phone.

According to another aspect of the embodiments of the invention, the master device used to perform the claimed method is a haptic device. As used in the present disclosure, "haptic technology" or "haptics" is a tactile feedback technology which recreates the sense of touch by applying forces, temperatures, vibrations, or motions to the user. This mechanical stimulation can be used to assist in the creation of virtual objects in a computer simulation, to control such virtual objects, and to enhance the remote control of machines and devices (telerobotics). Haptic devices may incorporate sensors that measure forces, pressures or movements exerted by the user on the interface. Haptic technology has made it possible to investigate how the human sense of touch works by allowing the creation of carefully controlled haptic virtual objects. These objects are used to systematically probe human haptic capabilities, which would otherwise be difficult to achieve. These research tools moreover contribute to the understanding of how touch and its underlying brain functions work. In a particular embodiment, the master robotic device can be a haptic device such as the PHANTOM Omni® Haptic Device or the like.

According to still another aspect, the slave device comprises a tapping/stroking device having at least two degrees of freedom (hereinafter, "DOF"), preferably three DOF. The slave device may comprise two mechanisms such as a belt-drive mechanism and a parallel-link mechanism. The belt-drive mechanism can be used e.g. for long stroking in which the belt linked with a direct-drive motor drives a carrier comprising an end link (such as e.g. a tubular shaft) on a linear guide in Y direction. Meanwhile, the parallel-link mechanism may enable both the tapping and stroking in X and/or Z directions. The motors can receive the command voltages from a computer via PCI data acquisition cards. The end link, for example a carbon-fiber tube, can be removed and replaced with other components. Additionally, the slave device (and/or the master device) can be equipped with sensors measuring physical (e.g. contact force) or physiological parameters (e.g. subject's body temperature). For instance, a load cell can be attached on the tip of the slave device in order to measure and feedback the contact force to the master device. This information can also be possibly manipulated (e.g. delayed or magnified in the case of a force) and displayed to the subject by the master device, or even recorded by any suitable way for e.g. further analysis in a therapeutic use. Accordingly, according to another aspect, a method can be provided for inducing the FoP, and further comprises the step of recording physical or physiological signals from sensors placed on the slave device.

Miniaturized versions of the slave device can be imagined, as well as wearable or even body implantable slave devices for more tailored and precise control thereof. For instance, ad hoc clothes such as pants, jackets, helmets, hats and the like can be imagined, including miniaturized versions of the slave device therein, to be worn in situations when a FoP is required or desired.

A further suitable variant with respect to the slave device includes robotic apparatuses which do not directly touch the subject's body, but are however able to induce a contact feeling to the subject. A simple example relies in a slave device able to release air flows from the tip of a tubular element: in this case, the robotic slave apparatus does not directly come into physical contact with the subject's body, but the subject is anyway able to perceive a tactile sensation induced by the air flow.

One of ordinary skill in the art will appreciate that more than one master device and/or more than one slave device can be used in order to put in place the method according to an aspect of the invention. This would be useful to induce several kind of FoP depending on the master(s)-slave(s) spatio-temporal relationships. For instance, it can be envisaged a configuration in which more than one limb (or extremity)-connected master device activates several slave devices in connection with several subject's body parts. By synchronising in many different ways the movements of the masters and the slaves in synchronous/asynchronous and/or symmetric/asymmetric fashion, the feeling of a presence (or more than one presence) can be induced in the subject, in different locations in the subject's surrounding space and in different moments.

Many industrial applications can be envisaged for the device, system, and method according to the embodiments of the present invention. The induction of the feeling of one or more presence/person can be implemented as an additional feature in several video-related experiences in order to render them more realistic and vivid. For instance, the FoP can be experienced, or could be experienced if desired, by cinema audience, or by private users desiring to immerse themselves in a more intense way into a video call, movie, 3D movie or a hologram-based video projection, in order to boost the feeling of really being inside the scene and in the presence of someone else.

The induction of a FoP through the present device, system, and method can be also implemented in videogames or virtual reality settings so that the impression of being in real contact with someone is enhanced and ameliorated. Videogame users of war, sport, first person shooter or survival/horror videogames, just for citing a few examples, could benefit from a method for inducing FoP in order to have a more striking and powerful game experience. In virtual reality environments, including role games or any other kind of simulation, the FoP could help in sensing e.g. team players or enemies in the subject's proximity, therefore improving for instance subject's reactivity or reflexes, while giving a stronger feeling of immersion within the environment.

Turning on biomedical aspects, the present device, system, and method can be useful for studying and deepening the understanding of the mechanisms behind the generation of the experience of "self" and "other", especially when this is distorted or altered in psychiatric or psychotic patients.

As used herein, the "term psychiatric" means related to or pertaining to psychiatry. Psychiatry is a field of medicine focused specifically on the mind, aiming to study, diagnose, prevent and treat mental disorders in humans, which include various affective, behavioral, cognitive and perceptual abnormalities.

As used herein, the term "psychotic refers to people experiencing psychosis. "Psychosis" is an abnormal condition of the mind, and is a generic psychiatric term for a mental state often described as involving a "loss of contact with reality". Psychotic subjects may exhibit some personality changes and thought disorder. Depending on its severity, this may be accompanied by unusual or bizarre behavior, as well as difficulty with social interaction and impairment in carrying out daily life activities. The term psychosis is very broad and can mean anything from relatively normal aberrant experiences through to the complex and catatonic expressions of schizophrenia and bipolar type 1 disorder. In properly diagnosed psychiatric disorders, psychosis is a descriptive term for the hallucinations, delusions, sometimes violence, and impaired insight that may occur. Psychosis is generally given to noticeable deficits in normal behavior (negative signs) and more commonly to diverse types of hallucinations or delusional beliefs, especially as regards the relation between self and others as in grandiosity and pronoia/paranoia.

The induction of FoP and related robot-controlled bodily illusions could be used as a diagnostic marker for the development of positive symptoms in schizophrenia. This is based on the fact that, during the robot-controlled induction of FoP, first-rank patients respond differently, both subjectively and behaviorally, than other schizophrenic patients and healthy controls. The induction of a FoP through the method can be also implemented in order to develop or refine rehabilitation or prosthetic approaches for the treatment of mental disorders in patients suffering from psychiatric diseases. For example, patients suffering from schizophrenia and hallucinations can undergo rehabilitation training where the conditions that lead to the FoP are systematically mapped and then translated into rehabilitation settings where exposure to specific time delays between the master device movement and the slave device response, decreases the strength of hallucinations that are difficult to treat by pharmacological agents, but intrinsically linked to the FoP (such as auditory verbal hallucinations, thought insertion, thought withdrawal). In the prosthetics scenario, patients suffering from schizophrenia and hallucinations would be envisaged using a wearable master-slave systems able to track selected actions of the patient and provide appropriate feedback in real-time. Both approaches could be applied in order to down-regulate acute hallucinations and other psychotic symptoms and also be exploited to achieve prophylactic effects.

In this context, the present device, system, and method can be used even in a diagnostic settings wherein invasive or non-invasive brain imaging techniques (such e.g. Magnetic resonance imaging, MRI; electroencephalography, EEG; near-infrared spectroscopym, NIRS; electrocorticography, ECoG) or brain stimulation techniques (e.g. Transcranial magnetic stimulation, TMS; transcranial direct-current stimulation, TDCS; transcranial pulsed ultrasound, TPU) are performed before, during or after a subject undergoes the present device, system, and method for inducing FoP. For instance, the robotic master-slave system can be designed and developed to be MRI compatible, so that MRI scan images can be acquired while the subject is induced to experience a FoP. In such a scenario, some expedient or precaution should be taken in order to have reliable and trustworthy results from the experiments; for example, the slave device must be designed to interact with the body in a highly limited space, since little space can be found between human back and a bed of MRI scanner, and all the components should be made of non-magnetic materials, such as polyacetal, brass, aluminum etc., in order to avoid or reduce safety and signal noise issues.

The induction of a FoP through the present device, system, and method can be also implemented to manipulate other aspects of self-consciousness, such as the sense of thought ownership, thought agency, and judgments about the number of thoughts in a human person's mind. The present device, system, and method can thus empower users with the potential to measure and manipulate the number of thoughts in the subject's mind, potentially leading to the development of robotic procedures to enhance creativity.

Next, different examples are provided to explains the various embodiments of the present invention.

In a first example that can correspond to one embodiment of the robotic device, system, and method, a commercial master haptic interface is used, the Phantom Omni (SensAble Technologies), and a three degree-of-freedom (DOF) slave robot, as shown in FIG. 1. The slave device consists of two mechanisms: a belt-drive mechanism and a parallel-link mechanism. The belt-drive mechanism is made up of a belt linked to a direct-drive DC motor (RE 40, Maxon™) moving a carrier on a linear guide allowing movements in the y (forward-backward) direction. The parallel-link mechanism is actuated through two harmonic drive motors (RH-8D 6006, Harmonic Drive Systems) and enables both tapping and stroking in x (right-left) and z (up-down) directions. These three motors equipped with optical encoders for positions sensing are connected to motor drivers (4-Q-DC Servoamplifier LSC 30/2 & ADS 50/5, Maxon) that receive the command voltages from a computer via PCI data acquisition cards (NI PCI-6221 & NI PCI-6014, National Instruments™). The overall workspace of the slave device is 200 mm in the x direction, 250 mm in the y direction, and 200 mm in the z direction.

A load cell (ELPFTIM-50N, Measurement Specialties) can be attached to the tip of the slave device in order to measure contact force. This allows to introducing a compliance factor on the system preventing the slave device from applying instantaneous strong force to the subject, making the interaction safer and more realistic. The system was controlled through an application programmed in Visual C++ (Microsoft™) at a sampling rate of 1 kHz. The latency related to information transfer delays and computational processing necessary for mapping the master device movements to the slave device movements (i.e. touching the back of the participants) was equal to 1 ms (delay for the near-synchronous condition in experiments using movement). Movements were always guided by the subjects. The system had a bandwidth of approximately 2.5 Hz allowing a good synchrony (delay=1 ms) between the master and the slave even during rapid and abrupt changes in velocity and direction. This allowed reducing the constraints on subjects' movements.

Figure 2:
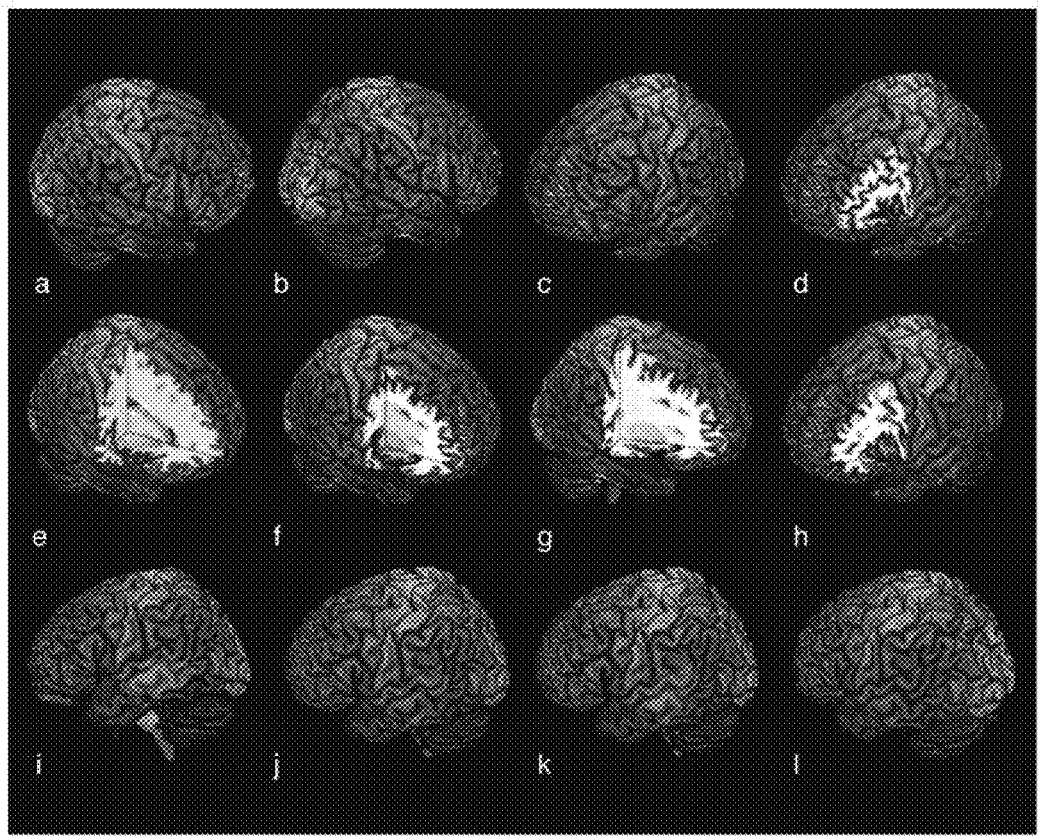
FIG. 2 depicts individual lesion data, i.e. the brain lesion separately for each of the twelve (12) tested FoP-patients.

In a second example, the results thereof can correspond to another embodiment of the present invention, related to the neurology andtheFoP, experimental tests were performed for lesion analysis and the associated hallucinations and neurological symptoms in 12 FoP patients were analyzed, as shown in Table 1, and FIG. 2.

Figures 3A, 3B:
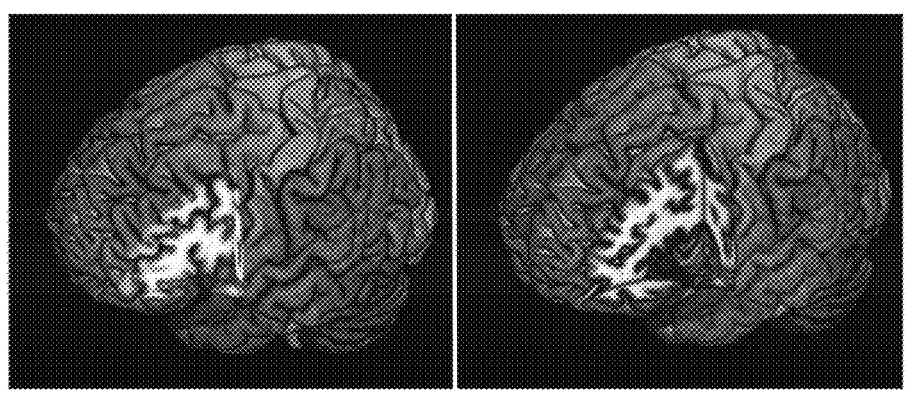
FIGS. 3A-3B depict (A) lesion overlap analysis for the FoP group, revealing three regions where overlap was maximal; (B) maximal lesion overlap for the control group.

The presence was felt in all cases in close proximity to and behind the patient's body ($p<0.01$). The presence was lateralized ($p<0.01$) in contralesional space ($p<0.01$) and equally often in right or left hemispace (not significant, n.s.; Table 1). Sensorimotor deficits ($p<0.01$) and the experience of illusory movements of the presence during movements of the patient (n.s.) were frequent symptoms. For lesion analysis, a multimodal imaging approach has been used, relying on combined functional and structural neuroimaging data to determine anatomical regions of maximal lesion overlap. This approach, which combined functional and structural lesion data, was necessary because many patients suffered from epilepsy, and in several patients, FoP was induced by electrical stimulation, and because the FoP is rare. Projecting all lesions onto the left hemisphere, lesion overlap analysis highlighted three cortical regions: insular cortex, frontoparietal cortex, and the temporoparietal cortex, as shown in FIG. 3A. Next, lesion extent within these three cortical regions between FoP patients and control patients matched for complex hallucinations, etiology, and sensorimotor deficits were compared as shown in FIG. 3B. Lesion extent did not differ between both groups in Brodmann area 22 ($p=0.18$) and 48 ($p=0.68$), whereas FoP patients had significantly larger lesions in Brodmann area 7 ($p=0.01$). These results show that although FoP is associated with insular, temporoparietal, and frontoparietal lesions, only frontoparietal lesions (Brodmann area 7) were specifically associated with the FoP.

TABLE 1

Clinical Data for FoP Group: Clinical Data Are Summarized for Each FoP Patient

| Patient | Diagnosis/Etiology | Lesion | Lesion Analysis | Neurology/Neuropsychology | Semiology |
|---|---|---|---|---|---|
| FoP a | neurocystcercosis | frontoparietal cortex (R) | MRI | gait disturbance/ mild executive deficits | presence of a person while walking, to his right, behind |
| FoP b | epilepsy, status post (s/p) ischemic stroke, vasculitis | occipitoparietal cortex, frontoparietal cortex (R) | MRI, EEG | left-sided sensorimotor deficit | presence behind left shoulder, a silhouette, like a shadow of the same proportions; echopraxia; unpleasant; most frequently perceived while walking |
| FoP c | epilepsy | frontoparietal cortex (L) | MRI, EEG, PET, SPECT, iEEG | right-sided weakness/postictal aphasia | presence of a "black person" behind her, no lateralization, unpleasant |
| FoP d | epilepsy, s/p resection of capillary angioma in the left insula | insula, frontoparietal cortex (L) | MRI, EEG, PET, SPECT, cortical stimulation | right-sided numbness/ executive deficits | presence of a man, behind to her right, in peripersonal space, fear and anxiety |
| FoP e | intracerebral hematoma, ischemic stroke | temporal lobe, frontal lobe, parietal lobe, insula (R) | MRI | left-sided sensorimotor deficit/anosognosia, reduplicative paramnesia | presence of daughter about 50 cm behind, to the right |
| FoP f | epilepsy, cerebral histiocytosis | thalamocapsular-caudate region, insula (R) | MRI, EEG | left-sided dysmetria/left spatial neglect | presence of "a person's black shadow" to her left, same position and posture as the patient, close family member |
| FoP g | epilepsy, s/p capsulolenticular haemorragic stroke | insula, capsulolenticular region (R) | MRI, EEG | right-sided paraesthesia and hemiparesis/neglect, apraxia | presence of four people in mostly left frontal space, family members |

TABLE 1-continued

Clinical Data for FoP Group: Clinical Data Are Summarized for Each FoP Patient

| Patient | Diagnosis/Etiology | Lesion | Lesion Analysis | Neurology/Neuropsychology | Semiology |
|---|---|---|---|---|---|
| FoP h | epilepsy, hemiplegic migraine | insula, parietooccipital cortex (L) | MRI, EEG | right-sided paraesthesia and weakness/aphasia | presence of a person's "shadow" to his right, behind |
| FoP i | epilepsy | mesial temporal lobe, anterior temporal lobe (L) | MRI, PET, SPECT, iEEG | normal/postictal aphasia | sensation of somebody's presence, behind to the left, anxiety |
| FoP j | epilepsy, s/p resection of a left temporal dysplastic lesion | temporoparietal cortex (L) | MRI, EEG, PET, SPECT, cortical stimulation | normal/aphasia, anomia | presence of a male shadow, behind to the right, same position, echopraxia |
| FoP k | epilepsy | posterior temporal lobe (L) | MRI, cortical stimulation | normal/aphasia | presence behind to the right, strictly unilateral, unpleasant, no echopraxia |
| FoP l | epilepsy, intracerebral hematoma | temporoparietooccipital cortex (L) | MRI, EEG | right sided sensorimotor deficit/aphasia, paraphasia, agraphia, alexia | presence of a person ("shadow of a female person"), on her right side (20-30 cm), behind, while standing and walking, echopraxia |

Figure 4A:
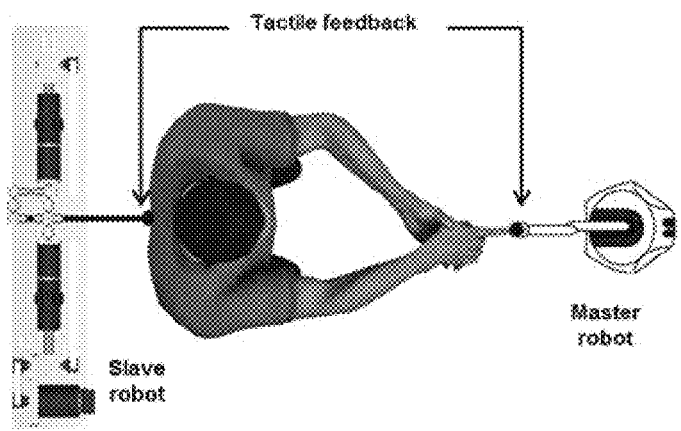
FIGS. 4A-4C depict the Master-Slave Robotic System and Tactile Full-Body Illusion, according to another aspect. (A) Schematic view of the master haptic interface (Phantom Omni; SensAbleTechnologies) and the slave robot. (B) Ratings for illusory touch and control questions. Illusory self-touch is significantly larger in the synchronous versus asynchronous condition (p<0.01) and also significantly larger than ratings of the control items (p<0.01). (C) Participants showed a drift in self-location toward the virtual back (toward the fingertip) that was larger during the synchronous than asynchronous conditions (p<0.01) and was larger in the condition with versus without somatosensory force feedback to the participants' fingertip (p<0.05). Self-location was quantified using the mental ball throwing task, during which participants were asked to estimate (by pressing a button) the time that a ball they were holding in their hands would take to reach the wall if they were to throw it. The condition in which five subjects spontaneously noted a FoP is indicated with an arrow. Error bars show the SEM.

According to another aspect, with Example 4, robotically induced bodily illusions were tested and the results evaluated. In order to study the FoP in healthy subjects, a master-slave robotic system has been designed and sensorimotor signals and their role in inducing FoP experimentally were investigated by integrating findings with principles from other body illusions. For these experimental results, informed consent was obtained, and all the studies were conducted in conformity with the Declaration of Helsinki. It was investigated whether the FoP is associated with illusory touch sensations, by using questionnaires, and mislocalization of the body, see FIG. 4A, FIG. 1. While standing and blindfolded, participants moved their arms and thereby moved the master device (via their inserted right index fingers) in front of them. These movements were sent to the slave robot, which applied tactile stimuli in real time to the participants' backs, see FIG. 4A. Participants moved the master robot for 3 minutes while they received tactile cues on their backs (by slave robot) and their right fingertips (by master robot). Stroking was applied either synchronously or asynchronously (500 ms delay), with or without somatosensory force feedback at the hand (2×2 factorial design).

Figure 4B:
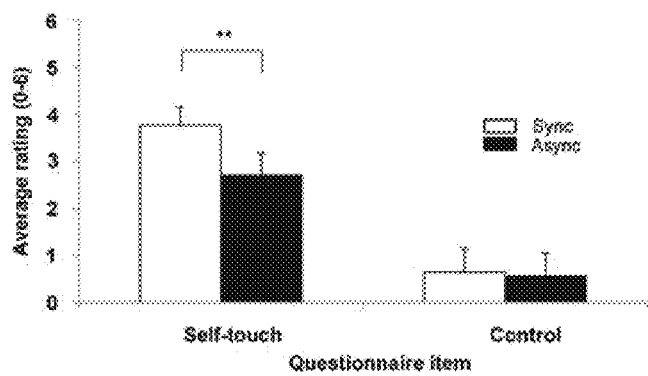
Figure 4C:
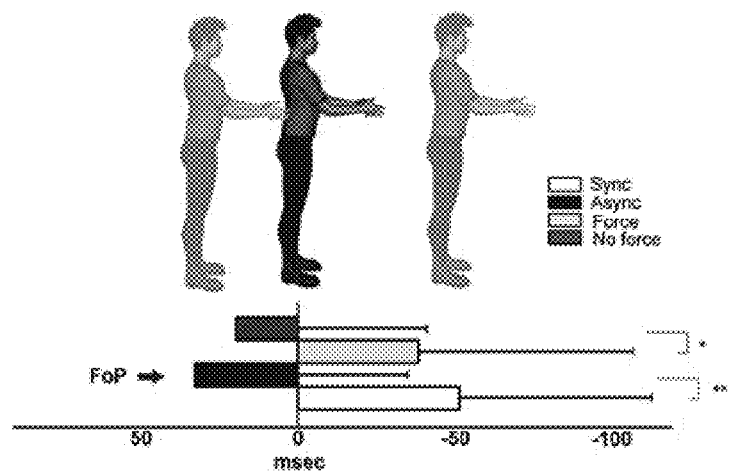

During synchronous, but not asynchronous, stimulation, participants experienced the sensation of touching themselves (self-touch), despite extending their arms in front of their bodies (p<0.01; see FIG. 4B). Synchronous stimulation and stimulation with force feedback were further associated with a drift of the subject's body toward the front position, where they felt their hands (p<0.05; see FIG. 4C). Thus, sensorimotor signals from the fingertip (forward-extended arm) while a tactile cue is applied to the subject's back induce the illusory feeling of touching one's own back with one's own finger (self-touch) and bias self-location toward the fingertip. These findings extend earlier illusions due to sensory conflicts between two hands or between two hands and the nose to an illusion between hand and trunk.

Figure 5A:
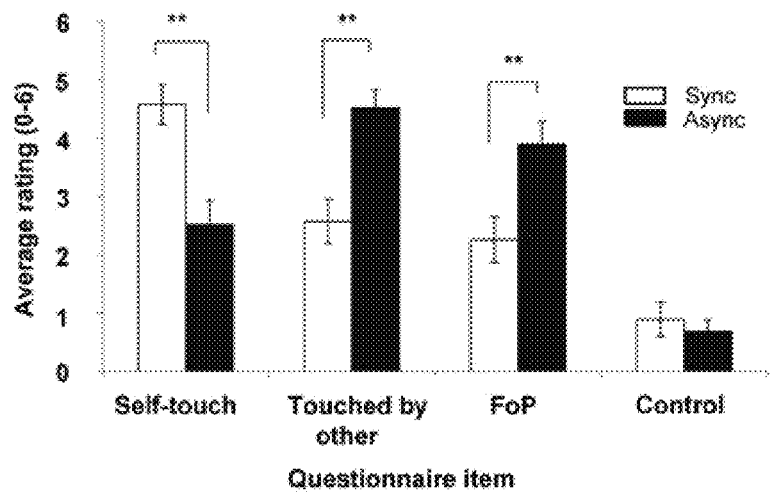
FIGS. 5A-5C depict the Robotically Induced FoP. (A) FoP questions, touched-by-other questions, illusory self-touch questions, and control questions are shown. As predicted, during asynchronous stimulation, participants experienced another person standing behind them (FoP; p<0.01), touching them (touched by other; p<0.01). Synchronous stimulation induced illusory self-touch (p<0.01). (B) A significant difference in self-location was found between the asynchronous (backward direction, associated with FoP) and synchronous condition (p<0.05). (C) Number of people (0-4) that participants judged as being close to them (the following question was asked: "how many people do you feel close to you?"; person numerosity task) during synchronous and asynchronous sensorimotor stimulation. As predicted, participants reported a significantly higher number of people during the FoP condition (asynchronous) than the synchronous condition (p<0.01). During the experiment, no human being was ever close to the participants.
Figure 5B:
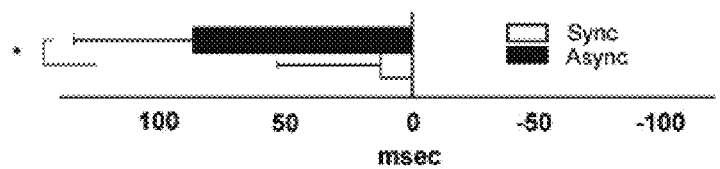
Figure 5C:
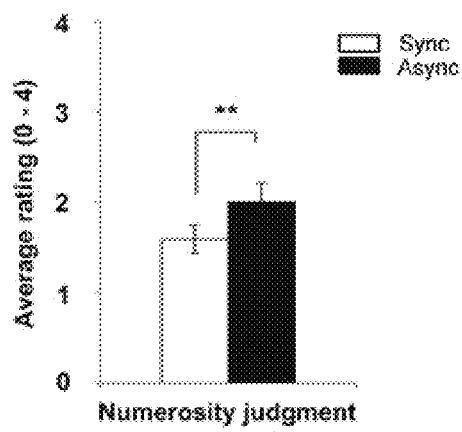

Next, Example 4 is provided as another aspect of the embodiments, with a robotically induced FoP. More interesting effects were observed during stronger sensorimotor conflicts; during asynchronous stimulation, participants showed a drift in self-location in the opposite, backward direction (p<0.01) and reported higher other touch than self-touch. Moreover, during post condition debriefing, five subjects reported to have experienced a FoP. In one experiment, it was investigated whether they could induce the FoP experimentally, predicting that under asynchronous stimulation without somatosensory force feedback (fingertip), subjects would feel the presence of a person that is touching them, associated with a backward drift in self-location (toward the presence). FIG. 5A shows that participants experienced being in the presence of another person in the asynchronous versus synchronous stimulation condition (p<0.01) and experienced being touched by that invisible presence behind them (p<0.01). Asynchronous stimulation induced a backward drift in self-location toward the position of the presence (p<0.05; FIG. 5B). To exclude that the FoP was caused by explicit questioning or related mechanisms, for the experimental tests, a person numerosity task was designed that tested implicitly the presence of another person close to the participant. While using the robot in synchronous and asynchronous stimulation, participants estimated the number of people that they felt close to them in the testing room (the following question was asked: "how many people do you feel close to you?"). Data show that during the asynchronous (FoP-inducing) condition, participants judged a significantly higher number of people as being close to them (mean=2.0) as compared to the synchronous condition (mean=1.6; p<0.01; FIG. 5C).

The neurological data reveal that the FoP is caused by focal brain lesions and that the FoP is most often experienced unilaterally, within peripersonal space behind the body, and associated with illusory own-body perceptions. FoP patients also show frequent somatosensory-motor deficits that were contralateral to the lesion on the same side as the presence. Compatible with the variability in lesion location across earlier clinical studies, it has been found that lesions associated with the FoP were focal but were linked to temporoparietal, frontoparietal, and insular cortex (of either hemisphere). Previous work showed that brain interference or lesions in FoP patients were in temporoparietal cortex and frontoparietal cortex. The data also highlight that the FoP follows insular lesions and indicated lesion location with greater precision than previous work.

Additional analysis in control patients (matched for complex hallucinations, etiology, and sensorimotor deficits) revealed that from the three lesion-overlap zones, only the frontoparietal site was specifically associated with the FoP, highlighting the importance of the latter region in the FoP.

Interestingly, temporoparietal cortex, insula, and frontoparietal cortex have been associated with bodily self-consciousness and are areas that integrate sensorimotor or multisensory bodily signals, as shown in human and non-human primates, compatible with the sensorimotor deficits herein observed. The present findings highlight that the FoP is characterized by its own distinct phenomenology (compared to out-of-body experiences, heautoscopy or autoscopic hallucinations) and interference with frontoparietal cortex. All latter conditions have been linked to a single and hemisphere-specific lesion site and to disorders of multisensory integration that do not involve the sensorimotor system. OBEs are attributed to visuosomatosensory-vestibular disintegration, heautoscopy is attributed to visuosomatosensory-interoceptive disintegration, and autoscopic hallucinations are attributed to visuosomatosensory disintegration. Instead, the present FoP data give most importance to abnormal integration of sensorimotor signals caused by frontoparietal lesions of either hemisphere. The robotic data corroborate and apply the neurological findings to healthy subjects and show that sensorimotor conflicts using well-controlled bodily stimulations are sufficient to induce the FoP. Based on clinical data and previous body illusion work, the robotic data show that the FoP can be induced when exposed to conflicting sensorimotor signals that are spatially and temporally incompatible with physical self-touch. Joining sensorimotor signals from forward-extended arms without force feedback at the fingertips (motor-proprioceptive cues), with delayed tactile feedback at the subjects' backs, was sufficient to induce the FoP. Under such stimulation, subjects reported being in the presence of another person behind them and being touched by that invisible presence. This was associated with a backward drift in self-location toward the presence and with elevated person numerosity judgments, corroborating experiential findings behaviorally.

The robotically induced FoP thus mimics the FoP in clinical populations and healthy subjects and is associated with abnormal perception of one's own body. These are major quantitative achievements because previous reports consisted of post hoc anecdotal accounts occurring far away from the research laboratory and because the FoP has never before been induced experimentally. A prominent model for motor control and bodily experience posits that efferent copy signals from the sensorimotor system are used to make predictions about the sensory consequences of movement and that such integration is fundamental for normal bodily experience. Predicted sensory consequences based on motor commands are compared with the reafferent sensory inputs during motor execution. A match between the predicted sensory information and the actual sensory information is considered to be self-generated, whereas differences between predicted sensory consequences and the reafferent signals are indicative of the influence of an external object or another agent.

The master-slave robot generated a spatiotemporal mismatch between participants' arm movements (motor-proprioceptive signals) and their sensory consequence (tactile feedback on their back), which was delayed and spatially incompatible with respect to the arm-related signals. This spatiotemporal conflict was resolved by the subjects by generating the illusory experience that the felt touch was not caused by themselves but by another person behind them who was touching their backs. This was revealed by subjective evidence, that is, a decrease in the reported feeling of touching one's own body, an increase in the feeling of being touched by somebody else, and an increase in feeling the presence of another person under asynchronous stimulation.

In addition to explaining a fascinating phenomenon with a rich cultural history, the present data are also of relevance for the understanding of schizophrenic symptoms. Abnormal integration of sensorimotor signals and their cortical representations has been described in schizophrenic patients and has been associated with positive hallucinatory and delusional symptoms. According to this view, positive schizophrenic symptoms, such as alien voices and delusions of control, are caused by central deficits in integrating predicted sensory consequences of own movements and the respective reafferent signals.

As a consequence, schizophrenic patients under certain conditions may not perceive self-generated sounds and movements as such but may misperceive them as being generated by external agents (as in the experience of alien voices or control of own movements by others). The present data not only account for a loss of agency in such patients but also show that a conflict between proprioceptive-motor signals and tactile feedback at a physically impossible position induced the feeling of being in the presence of an alien agent and being touched by that invisible person. Furthering the mechanistic insight into the functional brain processes generating hallucinations and delusions, the resulting experimental tests surprisingly show that simple sensorimotor conflicts induced, in healthy subjects, an experience that shares crucial aspects with positive, first-rank symptoms in schizophrenia, including the apparition of the alien agent.

Moreover, according to yet another aspect, Example 5 is provided, that tests and analyses robot-controlled auditory misattribution in first-rank schizophrenic patients. In a clinical study, it has been tested how sensorimotor conflicts, administered though the above-described robotic master-slave device, affect audio-verbal (AV) processing in first-rank schizophrenic patients (patients who presents psychotic symptoms, see below), and non-first-rank schizophrenic patients (patients without psychotic symptoms). To date, the categorization (diagnosis) of these different groups is based on patient's interview rather than more objective and reliable measures.

Regarding the participants, thirty one individuals in the early phase of psychosis having met criteria for a psychotic episode according to the Comprehensive Assessment of At-Risk Mental States criteria (mean (SD) age, 26.39 (±4.6) years; 9 women) were recruited to take part to this study. All the participants were included in the TIPP program (Treatment and early Intervention in Psychosis Program), a 3-year program launched in 2004 in Lausanne, at the Centre Hospitalier Universitaire Vaudois "CHUV", Switzerland, and dedicated to the intervention in the early phase of psychotic disorders. Twenty age matched controls subjects (mean (SD) age, 25.95 (±4.7) years; 5 women) from the control cohort of the TIPP program were recruited to take part to this study. They were assessed and selected with the Diagnostic Interview for Genetic Studies. Major mood, psychotic, or substance-use disorder and having a first-degree relative with a psychotic disorder were exclusion criteria for controls.

Exclusion criteria for the study were history of neurological illness or trauma, non-psychiatric visual or auditory disorders, diagnosis of psychosis related to intoxication or organic brain disease, intelligence quotient <70, age below 18 and above 35 at the TIPP inclusion, or antipsychotic medication more than 6 month before the inclusion. 90.3% of the subjects were right-handed.

Symptom severity and classification were assessed in the patient group using the Positive and Negative Syndrome Scale (PANSS) for schizophrenia. They scored a mean (SD) of 13.72 (±4.99) on the positive subscale, 13.72 (±4.71) on the negative subscale and 24.62 (±7.2) on the general psychopathology subscale. Patients were sorted according to the presence of first rank symptoms (FRS) (i.e. verbal hallucinations, impressions that another agent was controlling actions and thoughts, that thoughts have been stolen or introduced in the patient's mind or that someone else knows his thoughts). They were considered to have FRS if they presented at least one FRS during the psychotic episode, as defined by the glossary (1. audible thoughts, voices commentary, voices conversing/arguing, 2. thought insertion, 3. somatic passivity, 4. thought withdrawal, 5. thought broadcasting, 6. delusional perception, 7. made impulses, made volitional acts, 8. made thoughts/feelings). The patient underwent clinical assessment by a trained psychiatrist in 1-hour interview. A Schneiderian score was calculated for each patient by using a 1-7 rating scale according to the severity and by adding each of the eight items. Nineteen (19) subjects had a score greater than zero and were included in the FRS+ group; the mean value (maximum score=48) was 17.52 (±9.32) (range 5-33). Twelve (12) patients never presented first rank symptoms and had a zero score and were included in the FRS− group. The two groups were demographically similar in terms of age and level of education. However, although there were no differences between the two groups in the global clinical features (total PANSS and SIPS scores) and treatment duration, there were an expected significant difference in the positive PANSS subscore (related to first rank symptoms) and the chlorpromazine equivalent medication (used to treat first rank symptoms).

Twenty-seven (27) patients were medicated at the time of the study. All of these patients were prescribed atypical antipsychotic medications (amisulpride [n=5], lurasidone [n=1], olanzapine [n=1], quetiapine fumarate [n=10], risperidone [n=4], aripiprazole [n=6], paliperidone [n=1]) at time of participation. The chlorpromazine equivalent of antipsychotic medication dosage was observed to be a mean (SD) of 268.73 (±185.26) mg/d of chlorpromazine. At the time of the experiment, 19 patients satisfied the Diagnostic and Statistical Manual of Mental Disorders (Fifth Edition) (DSM-V) criteria for schizophrenia, 2 for schizoaffective disorders, 1 schizotypical disorders, 6 acute and transient disorders, 3 severe depressive episode and 1 bipolar disorder). All were clinically stable at the time of testing and gave written informed consent to participate in the study, which had been approved by the local Ethics Committee (CHUV, Lausanne). They were given a monetary inconvenience allowance for participation in the study. Informed written consent in accordance with out institutional guidelines (protocol approved by the Ethic Committee of Clinical Research of the Faculty of Biology and Medicine, University of Lausanne, Switzerland) was obtained for all participants.

Next, experimental tests on auditory misattribution have been performed. As auditory stimuli, participants were recorded while reading aloud a list of 50 common French words taken from Jalenques et al. ("Valence émotionnelle des mots dans la schizophrénie," L'Encéphale, Vol. 39, pp. 189-197, 2013) and controlled for valence and frequency. To make the words more difficult to recognize pink noise was added to the recordings using Matlab.

The following procedure was undertaken. While standing and blindfolded, participants moved their right arm thereby moved the master device, via their inserted right index fingers, in front of them. These movements were transferred to the slave robot, which applied tactile stimuli in real time to the participants' backs. Participants moved the master robot for 1 minute while they received tactile cues on their backs (by slave robot) and auditory stimuli via headphones type. Stroking was applied either synchronously or asynchronously (500 ms delay) as previously used to induce sensorimotor prediction errors (Blanke et al., "Neurological and robot-controlled induction of an apparition," Current Biology, Vol. 24, pp. 2681-2686, 2014). While stroking their backs participants heard words in their own voice or that of a gender matched participant. Words were presented every 5 seconds and participants were required to report if the word was spoken in their own voice (Self condition) or in another person's voice (other condition). There were 25 words presented in each block and the synchrony of sensorimotor feedback was pseudo-randomized between subjects. There were four blocks in total (2 synchronous and 2 asynchronous).

Next, the results of the auditory misattribution have been provided. To test for changes in self-monitoring for AV stimuli, Dprime rates were submitted to a 2×3 ANOVA with the factor of synchrony (synchronous/synchronous) as a within subject factor and group (Healthy/FR+/FR−) as a between subject factor. Dprime is calculates as Dprime=Z (hit rate)−Z(false alarm rate), where function $Z(p)$, $p \in [0,1]$, is the inverse of the cumulative distribution function of the Gaussian distribution. A smaller Dprime means that the signals is more hardly detected.

Figure 6:
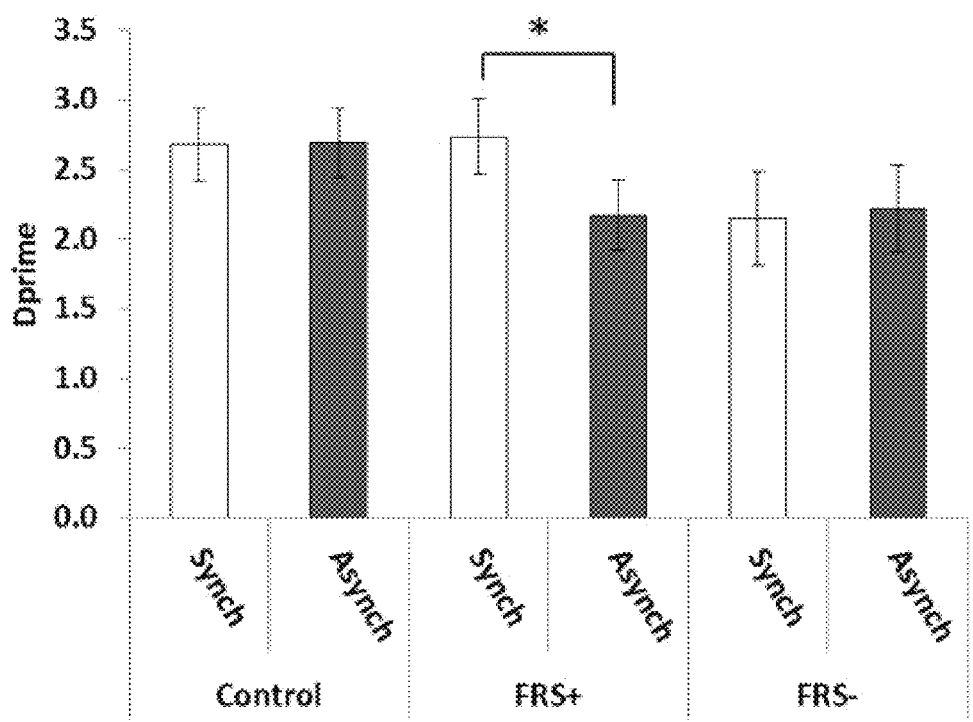
FIG. 6 shows a clinical study on robot-controlled auditory misattribution. Dprime score is shown for each group and each type of sensorimotor robotic stimulation. Note the significant Dprime reduction in the asynchronous sensorimotor stimulation only for the first-rank group.

The ANOVA revealed a significant interaction ($F(2, 38)=4.62$, $p=0.015$, partial $\eta 2=0.19$). Post hoc LSD analysis indicated that this was driven by a large drop in Dprime for the FR+ group in the asynchronous condition (M=2.17, 95% CI=+/−0.51) compared to the synchronous condition (M=2.73, 95% CI=+/−0.55, $p=0.0009$). There was no significant main effect of Group ($F(2, 38)=1.55$, $p=0.44$) nor any main effect of synchrony ($F(2, 38)=2.6$, $p=0.11$), see FIG. 6. The data show that the robot-controlled sensorimotor stimulation can be used to develop objective measures able to differentiate schizophrenic patients with psychosis (FRS+) from those that do not present psychotic symptoms (FRS−).

While the invention has been disclosed with reference to certain preferred embodiments, numerous modifications, alterations, and changes to the described embodiments are possible without departing from the sphere and scope of the invention, as defined in the appended claims and their equivalents thereof. Accordingly, it is intended that the invention not be limited to the described embodiments, but that it have the full scope defined by the language of the following claims.

The invention claimed is:

1. A method for inducing the feeling of an external human presence in a subject by using a master-slave robotic system, comprising:
   altering a visual perception of a surrounding environment of the subject;
   connecting the subject with a robotic master device so that the subject can move, move on or manipulate the robotic master device;
   connecting the subject with the robotic slave device such that the robotic slave device physically interacts with a trunk of the subject; and
   making the subject move, move on or manipulate the robotic master device so that the trunk of the subject is directly or indirectly touched by the robotic slave device according to a movement of the robotic master device to provide a stimulation,
   wherein the stimulation is such that the master device and the slave device are operatively connected such that the subject receives at least one of spatially and temporally conflicting sensorimotor stimulation.

2. The method of claim 1, further comprising the step of: recording physical or physiological signals from sensors placed on at least one of the robotic master device and the robotic slave device.

3. The method of claim 1, wherein the visual perception of the subject is altered by blindfolding the subject.

4. The method of claim 1, wherein the master device is a haptic device or a mobile device including a smartphone.

5. The method of claim 1, wherein the master device is connected to a limb or a limb extremity of the subject.

6. The method of claim 1, wherein the slave device is connected to a back of the trunk of the subject.

7. The method of claim 1, wherein at least one of the robotic master device and the robotic slave device are wearable.

8. The method of claim 1, wherein the robotic master device is a controller for a video device.

9. The method of claim 1, wherein the robotic master device and the robotic slave device are wirelessly connected.

10. The method of claim 1, further comprising the step of: analyzing a brain activity of the subject with at least one of invasive brain imaging, non-invasive brain imaging, and brain stimulation techniques.

11. The method of claim 1, further comprising the step of: treating or preventing at least some aspects of a psychiatric condition in the subject.

12. The method of claim 11, wherein the psychiatric condition is at least one of psychosis, schizophrenia, and hallucinations.

13. The method according to claim 12, wherein the robotic master device is a haptic device.

14. The method according to claim 12, further comprising a brain imaging device.

15. The method according to claim 1, wherein the stimulation is the temporally conflicting sensorimotor stimulation in which the robotic slave device is operated asynchronously with a temporal delay with respect to the robotic master device.

16. The method according to claim 15, wherein the temporal delay is at least 500 ms.

* * * * *